(12) United States Patent
Rydin et al.

(10) Patent No.: US 6,510,851 B2
(45) Date of Patent: Jan. 28, 2003

(54) METHOD AND ARRANGEMENT FOR EVALUATING EFFECTIVE FLOW RESISTANCE OF PATIENT BREATHING CIRCUIT

(75) Inventors: Göran Rydin, Täby (SE); Christer Ström, Pitea (SE); Johan Bennarsten, Gustavsberg (SE)

(73) Assignee: Siemens-Elema AB, Solna (SE)

( * ) Notice: Subject to any disclaimer, the term of this patent is extended or adjusted under 35 U.S.C. 154(b) by 35 days.

(21) Appl. No.: 09/892,025

(22) Filed: Jun. 26, 2001

(65) Prior Publication Data

US 2002/0020410 A1 Feb. 21, 2002

(30) Foreign Application Priority Data

Jun. 29, 2000 (SE) .............................................. 0002449

(51) Int. Cl.$^7$ ............................................. A61M 16/00
(52) U.S. Cl. ................................................. 128/204.21
(58) Field of Search ....................... 128/202.22, 204.18, 128/204.21, 204.23, 205.25

(56) References Cited

U.S. PATENT DOCUMENTS 5,876,352 A    3/1999  Weismann
6,257,234 B1 *  7/2001  Sun ........................ 128/204.18
6,390,091 B1 *  5/2002  Banner et al. ......... 128/204.21

OTHER PUBLICATIONS

"Estimation of Inspiratory Pressure Drop in Neonatal and Pediatric Endotracheal Tubes", Jarreau et al., Jarreau et al., J. Appl. Physiol., vol. 87, No., 1 (1999), pp. 36–46.

* cited by examiner

Primary Examiner—William C. Doerrler
Assistant Examiner—Malik N. Drake
(74) Attorney, Agent, or Firm—Schiff Hardin & Waite

(57) ABSTRACT

In a method and arrangement for evaluating effective flow resistance of a patient breathing circuit connected to a mechanical breathing assist device, a flow controller is operable to temporarily introduce an occlusion to the gas flow within the breathing circuit at a time after the end of an inspiration phase of a breathing cycle provided by the breathing assist device. A sensor unit 34 has a flow sensor for measuring gas flow within the circuit and a pressure sensor for measuring gas pressures within the circuit. An evaluating unit receives measurements from the sensor unit, to determine for a measured gas flow a value of a pressure drop within the breathing circuit after the introduction of the occlusion, and establishes a relationship between the calculated pressure drop and the measured gas flow, such as based on the known Blasius formula.

8 Claims, 5 Drawing Sheets

METHOD AND ARRANGEMENT FOR EVALUATING EFFECTIVE FLOW RESISTANCE OF PATIENT BREATHING CIRCUIT

BACKGROUND OF THE INVENTION

1. Field of the Invention

The present invention relates to a method for evaluating the effective flow resistance of a patient breathing circuit during mechanical breathing assistance and to a device for carrying out the method.

2. Description of the Prior Art

Providing mechanical breathing assistance to a patient is a well known medical procedure and is most often used in surgical and critical care situations. Typically, a breathing tube, such as an endotracheal or a tracheotomy tube, is inserted into the patient's trachea so that the distal end of the tube is disposed in the patient's airways and the proximal end is accessible external the patient. The proximal end connects with a gas tubing system, typically by means of a Y-piece connector, to form a breathing circuit which in turn connects with a breathing assist device. The breathing assist device, such as a ventilator, respirator or anaesthetic delivery system, is adapted to control the flow of gas through the breathing circuit to and from the patient's airways and thereby regulate the patient's breathing cycle.

Over-pressurization of the breathing gas provided to the patient through the breathing tube can cause barotrauma and therefore the gas pressure within the breathing circuit is usually monitored and used to control the assist device. Pressure sensors are typically provided within the assist device itself or at the Y-piece to monitor the gas pressures at the proximal end of the breathing tube. Because the breathing tube has a relatively narrow bore compared with the rest of the breathing circuit, the breathing tube presents a large resistance to gas flow. This leads to inaccuracies between the pressures registered by the sensors and those which exist within the lungs so that barotrauma may still occur due to a delivery pressure of the breathing gas that is too high. In other circumstances the delivery pressure of the breathing gas may be adjusted to a level that is too low so that efficient opening of the lungs no longer occurs.

In order to reduce the effects of the flow resistance of the breathing circuit (principally the delivery tube) on the safe and effective operation of the assist device it is known to adapt the device to compensate the sensed delivery pressure for the breathing tube resistance and to use this compensated pressure value to control the delivery of breathing gas. In known devices this is done by a user entering information relating to the breathing tube's resistance before the breathing assistance is started. This information may be in the form of the tube's length and internal diameter, from which a theoretical resistance can be calculated, or can be an actual calculated or measured resistance value determined before use.

A problem with this known approach is a possibility that the user may enter the information incorrectly. Another problem is that the resistance provided in the known manner may not be the true resistance of the tube since this may vary throughout the operation of the device or as a result of the initial placement of the tube within the patient's trachea.

SUMMARY OF THE INVENTION

An object of the present invention to provide a method and an arrangement for carrying out the method, which make it possible to alleviate at least one of the problems associated with known breathing assist devices.

This object is achieved in accordance with the present invention in a method for evaluating an effective flow resistance of a breathing circuit during mechanical breathing assistance wherein a pressure is measured in the breathing circuit and the breathing circuit is subsequently occluded, and a pressure drop as a result of the occlusion is measured. The resistance of the breathing circuit is then determined by establishing a relationship between the measured pressures before and after the occlusion.

The determined pressure drop at the onset of an occlusion may be assumed to effectively result from the resistance of a patient breathing tube which is present within the breathing circuit since the diameter of the tube is much smaller than the diameter of any other tubing component of the circuit. An indication of the tube resistance thus can be established from the pressure drop/flow relationship, which to a first approximation may be simply the determined pressure drop divided by the flow immediately before the introduction of the occlusion.

A method is disclosed in U.S. Pat. No. 5,876,352 based on the recognition that a pressure drop is dependent effectively on a patient's lung resistance and the compliance (resistance$^{-1}$) of the breathing circuit should be compensated for improving the accuracy of the described method.

Since the determined pressure drop effectively results from the patient tube resistance, then the known Blasius formula can then be used to provide, for a given gas flow F, a link between the determined pressure drop $\Delta P$, and the resistance R of the breathing tube of length L, and diameter D, according to:

$$\Delta P = 0.24 \times (L/D^{4.75}) \times \mu^{0.25} \times \rho 0.75 \times F^{1.75} \qquad (1)$$

wherein $\mu$ and $\rho$ are respectively the gas viscosity and the gas density.

Equation (1) may be re-written as:

$$\Delta P = K \times (L/D^{4.75}) \times F^{1.75} \qquad (2)$$

which gives $$\Delta P / F^{75-K \times (L/D^{4.75})} = R \qquad (3)$$

Thus by determining a pressure drop $\Delta P$ obtained at a flow value F, an indication of the effective resistance of the breathing tube can be obtained automatically during breathing assistance to avoid the need for user input of the information. In particular, from equation (3) a calculation of $\Delta P/F^{1.75}$ at a known flow or a calculation of a value of a linear rate of change of $\Delta P$ with $F^{1.75}$, that is, $d\Delta P/dF^{1.75}$, may preferably be used to provide an indication of the tube resistance.

Moreover the resistance is an actual resistance which thus reflects the reality of the breathing circuit in use. This has the advantage that the method may be employed to monitor the breathing circuit during mechanical breathing assistance for changes in resistance which would indicate a leakage (decreased resistance) or a blockage (increased resistance) or may be employed to provide a resistance value of the actual breathing circuit which is used to compensate pressure measurements made by sensors in the breathing circuit.

Preferably, the occlusions are introduced during an expiration phase of a patient breathing cycle so as to reduce the effect of the evaluation method on breathing gas supply to the patient and thus to reduce any discomfort which the patient might otherwise experience.

If the method is employed for a number of different gas flows, for example when calculating the flow dependent rate of change of pressure drop, that is either $d\Delta P/dF^{1.75}$ or $d\Delta P/dF$, then the different gas flows may be obtained by introducing the occlusions at different times within one or more expiration phases of a patient breathing cycle. Since the flow during an expiration phase varies with time, this has the advantage that the natural variation of flow with time over an expiration phase may be utilized to further reduce the adverse effects that the inventive method may have on the provision of mechanical breathing assistance.

The evaluation may be made at different times within a single expiration phase so that a calculation of the flow dependent rate of change of the pressure drop may be made in a single brething cycle. Alternatively, if a calculation is made during an inspiration phase of a single breathing cycle, then a ramped gas flow can be provided and occlusions similarly introduced throughout that phase.

The above-stated object also is achieved in accordance with the present invention in an arrangement for carrying out the above-described method.

DESCRIPTION OF THE PREFERRED EMBODIMENTS

Figure 1:
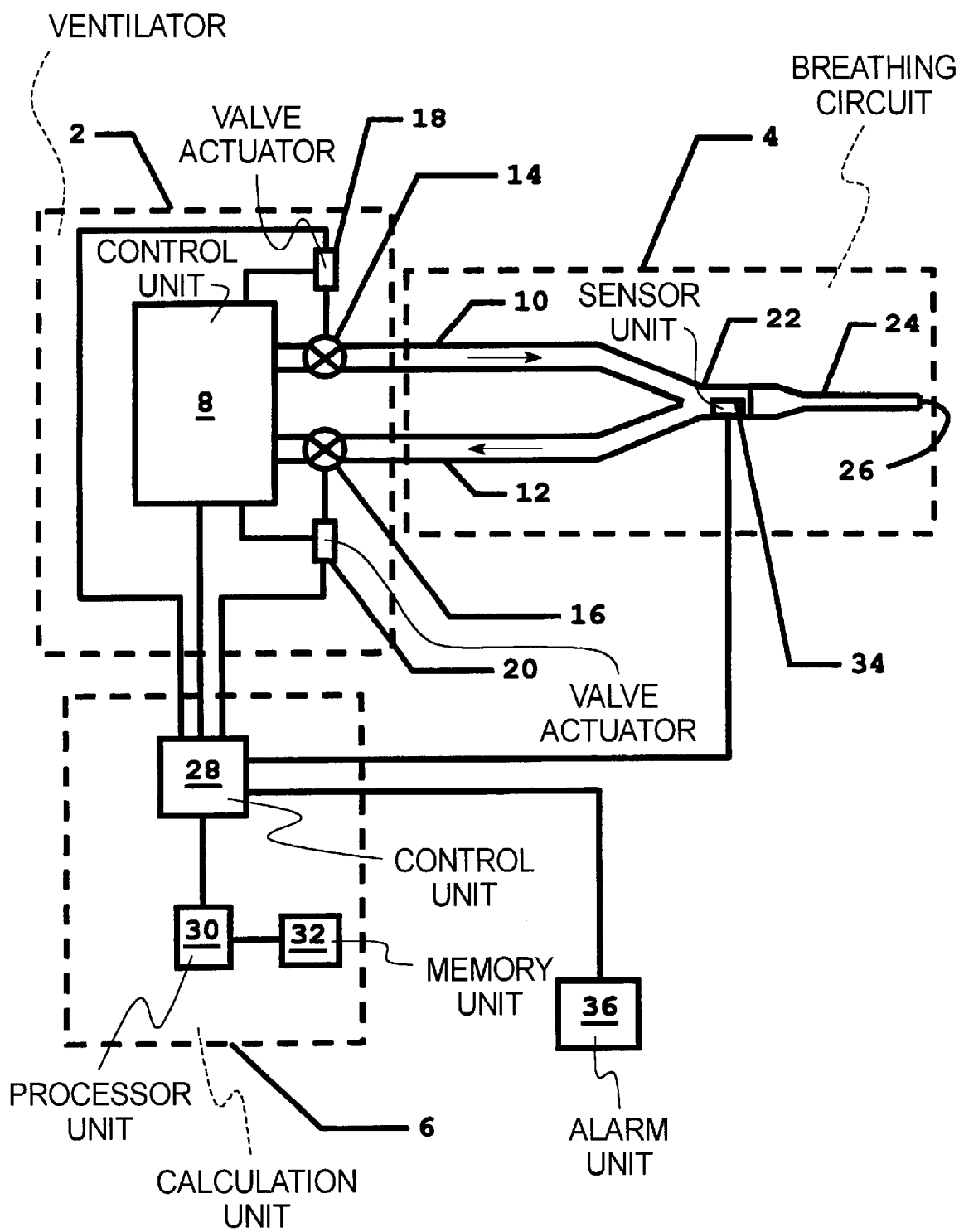
FIG. 1 is a schematic representation of an arrangement according to the present invention in operable connection with a mechanical breathing assist device.

FIG. 1 shows a patient ventilator 2 interconnected with a breathing circuit 4 and a calculation unit 6 for evaluating an effective flow resistance within the breathing circuit 2 during the assisted ventilation of a patient.

The patient ventilator 2 has a gas flow control unit 8 which connects to an inspiration line 10 and an expiration line 12 of the breathing circuit 4 via, respectively, an inspiration valve 14 and an expiration valve 16 within the ventilator 2. Valve actuators 18,20 within the ventilator 2 are operably connected to the inspiration valve 14 and the expiration valve 16 and operate on receipt of a control signal to open and close the associated valve 14 or 16. The flow control unit 8 is connected to the actuators 18,20 and provides control signals thereto in order to regulate the flow of inspiration and expiration gases in a known manner, to provide a mechanical breathing cycle having controllable inspiration and expiration phases during one or more known control modes of operation of the ventilator 2.

The patient breathing circuit 4 includes a Y-piece 22, the separate arms of which connect to the inspiration line 10 and the expiration line 12 and the common trunk of which connects to a small bore (typically between 5 mm and 8 mm) endotracheal tube 24. The endotracheal tube 24 has an open end 26 which, when breathing assistance is being provided by the ventilator 2, is inserted into the proximal airways of the patient.

The calculation unit 6 includes a control unit 28 and an operably connected processor unit 30 which has associated therewith a memory unit 32. It will be appreciated from the subsequent description of the operation of these units 28,30, 32 that they may be formed by a suitably programmed micro-computer. The control unit 28 is connected externally of the calculation unit 6 to a sensor unit 34, to the gas flow control unit 8, to the valve actuators 18,20 and to an alarm unit 36.

The sensor unit 34 has both pressure sensing and flow sensing elements and can be conveniently located within the common trunk of the Y-piece 22 so as to be able to monitor pressures and flows of both inspiration and expiration gases within the breathing circuit 4. The sensor unit 34 thus is able to provide the control unit 28 (and optionally the gas flow control unit 8) with measured values of pressure or gas flow for either of the inspiration gas and the expiration gas as required.

The control unit 28 is additionally operable to provide control signals to the valve actuators 18,20 to open and close the associated valves 14,16 and thereby introduce a temporary occlusion to gas flow within the breathing circuit 4. This may be achieved either directly or via the flow control unit 8, which normally operates to control these actuators 18,20 to provide a patient breathing cycle during normal operation of the ventilator 2. The control unit 28 may also can provide these control signals dependent on timing signals from the gas flow control unit 8 of the ventilator 2, which are synchronized with the inspiration and the expiration phases of the breathing cycle being provided by the ventilator 2.

In this manner valve components 14,18; 20,16 which are typically already found in the patient ventilator 2 for controlling inspiration gas flow and expiration gas flow during a patient breathing cycle may be employed in the present invention. Alternatively a specific valve arrangement (not shown) may be used to introduce occlusions to gas flow and may be placed at the Y-Piece 22 to reduce the number of extra components.

Figure 2:
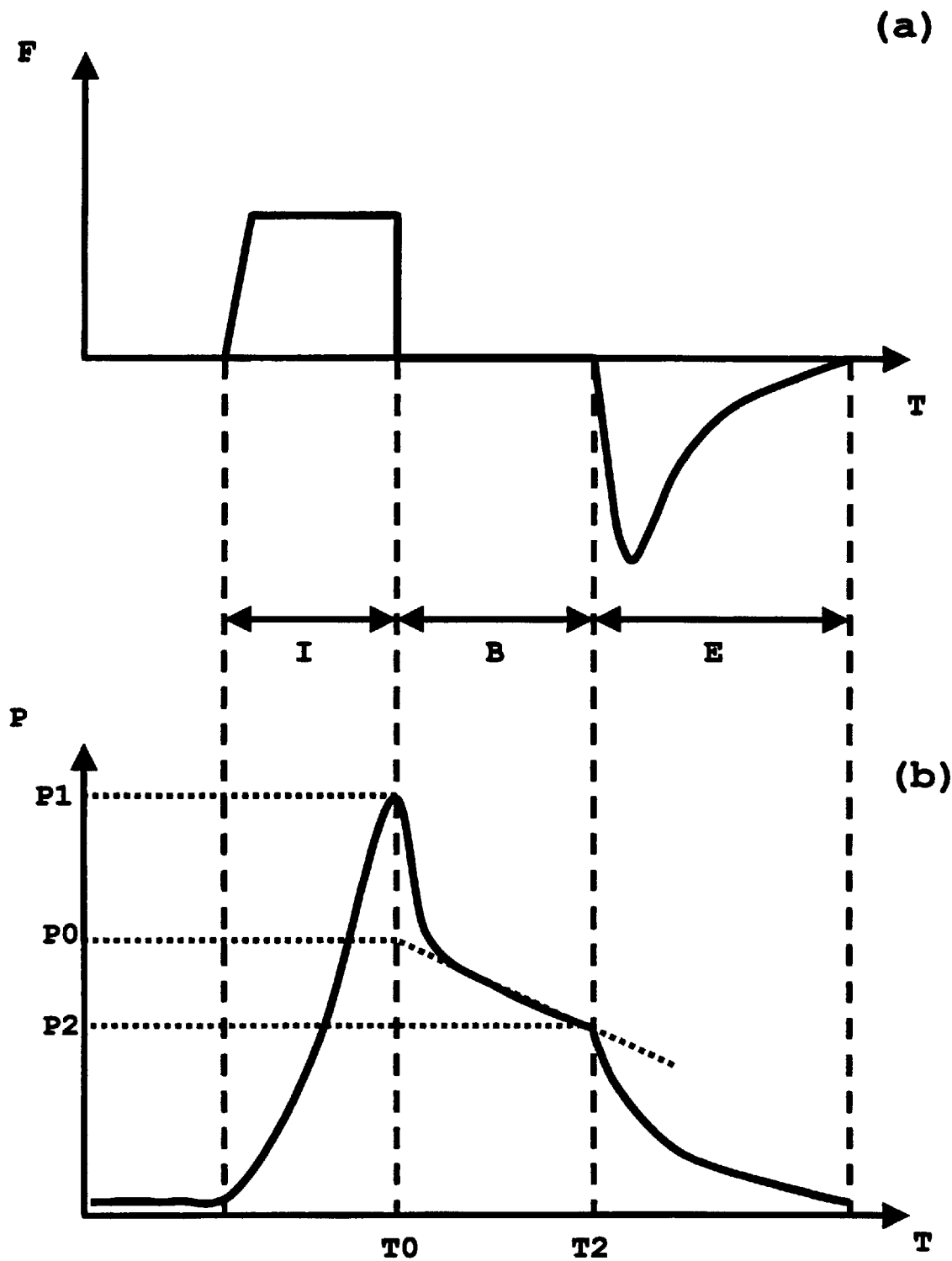
FIG. 2 illustrates in (a) gas flow characteristics during a volume control mode breathing cycle in which an occlusion is introduced as a breath-hold, and illustrates at (b) corresponding gas pressure characteristics.

During mechanical breathing assistance the effective flow resistance of the breathing circuit 4 can be evaluated as follows with reference to FIG. 2:

The gas flow control unit 8 of the ventilator 2 is arranged to provide in a volume control mode of operation a constant gas flow, F, to the patient during an inspiration phase, I. During this phase the inspiration valve 14 is open and the expiration valve 16 is closed under the control of the unit 8. At the end of an inspiration phase the unit 8 is instructed by the control unit 28 to also close the inspiration valve 14 and initiate a "breath-hold" B, at a time T0, and of a duration typically between 1 ms to 200 ms. After a predetermined time the control unit 8 is instructed to operate to open the expiration valve 16 and an expiration phase E, commences. The pressure P1, as measured by the sensor unit 34 immediately before the breath-hold B, is passed via the control unit 28 to the processor unit 30 where it may be stored in the memory 36 together with an associated gas flow value F, as also measured by the sensor unit 34. The pressure measurement is repeated throughout the duration of the breath-hold B and the "intermediate" pressure values are stored within memory 32 together with their associated times. A final pressure P2, is recorded at a time T2, at the end of the breath-hold and both values are again stored within the memory 32. The stored pressure and times are then accessed by the processor unit 30 which is adapted to calculate a pressure P0, being extant within the breathing circuit 4 immediately upon introduction of the breath-hold at time T0. This may be done by using the intermediate pressure and time values to obtain a gradient value with which to back-extrapolate the final pressure P2, which exists at T2, to the time T0. The difference between the pressures immediately before (P1) and immediately after (P0) the breath-hold B is taken to be the pressure drop $\Delta P$ resulting from the breathing circuit resistance, which is substantially due to the resistance of the endotracheal tube 24. The values $\Delta P$ and F are stored within the memory 32 and the process may be repeated at least once more with the flow-control unit 8 operating to provide a different value of inspiration gas flow, F. The processor unit 30 then operates to recall the stored $\Delta P$ and F values and evaluate an effective flow resistance using these recalled values. The unit 30 may be programmed to determine a relationship between the pressure drop $\Delta P$, and the (obtained flow values F)$^{1.75}$, such as by calculating a value of a linear rate of change of determined pressure drop with (obtained flow value)$^{1.75}$. This value, as can be seen from equation (3) above, provides a measure of the effective resistance of the breathing circuit 4.

Figure 3:
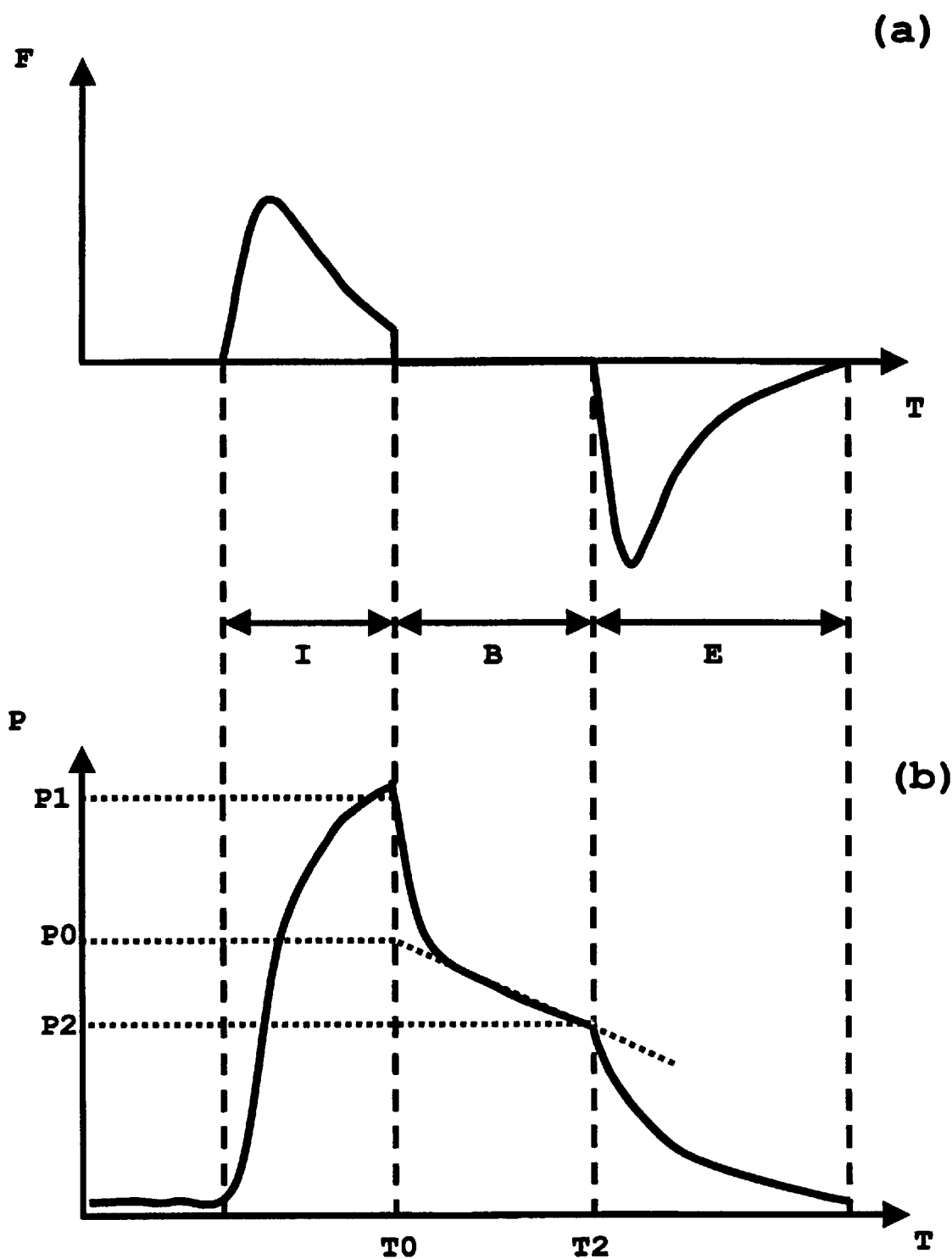
FIG. 3 illustrates at (a) gas flow characteristics during a pressure support mode breathing cycle in which an occlusion is introduced as a breath-hold, and illustrates at (b) corresponding gas, pressure characteristics.

It will be appreciated that the breath-hold technique may be applied in other operating modes of the ventilator 2. An example of this is provided for a pressure support mode of operation and is illustrated in FIG. 3 in which features common with FIG. 2 are given the same reference labels. During pressure support mode the ventilator 2 is operated in a known fashion to support a patient's breathing effort by supplying breathing gas upon receipt of a trigger signal from the sensors in the sensor unit 34 indicative of a patient attempting to breathe. Portion (a) of FIG. 3 illustrates a typical flow characteristic over one breath during pressure support and shows a varying flow during inspiration I. The breath hold B, is initiated based on an average of previous, typically three, breaths. The unit 8 operates to close flow valves 14,16 at a time T0 when a measurable quantity, such as inspiration time, inspiration flow, delivered volume, or inspiration pressure, in the present breath reaches a threshold based on the aforementioned average breath. Such a criteria for initiation a breath hold may be when the delivered volume reaches 90% of the expected total delivered volume based on an average of three preceding breaths. The calculations unit 6 then operates as described above with regard to the volume control mode of FIG. 2 to measure a final pressure P2, at the end of the breath hold at time T2 and to extrapolate back to determine a pressure P0 at time T0. The pressure drop $\Delta P$, being P1–P0, is calculated and a tube resistance R is determined from equation (3) above. Indeed if only an indication of tube resistance is required, for example if monitoring for changes in measured resistance, then a relationship of $\Delta P/F$ need only be determined.

Figure 4:
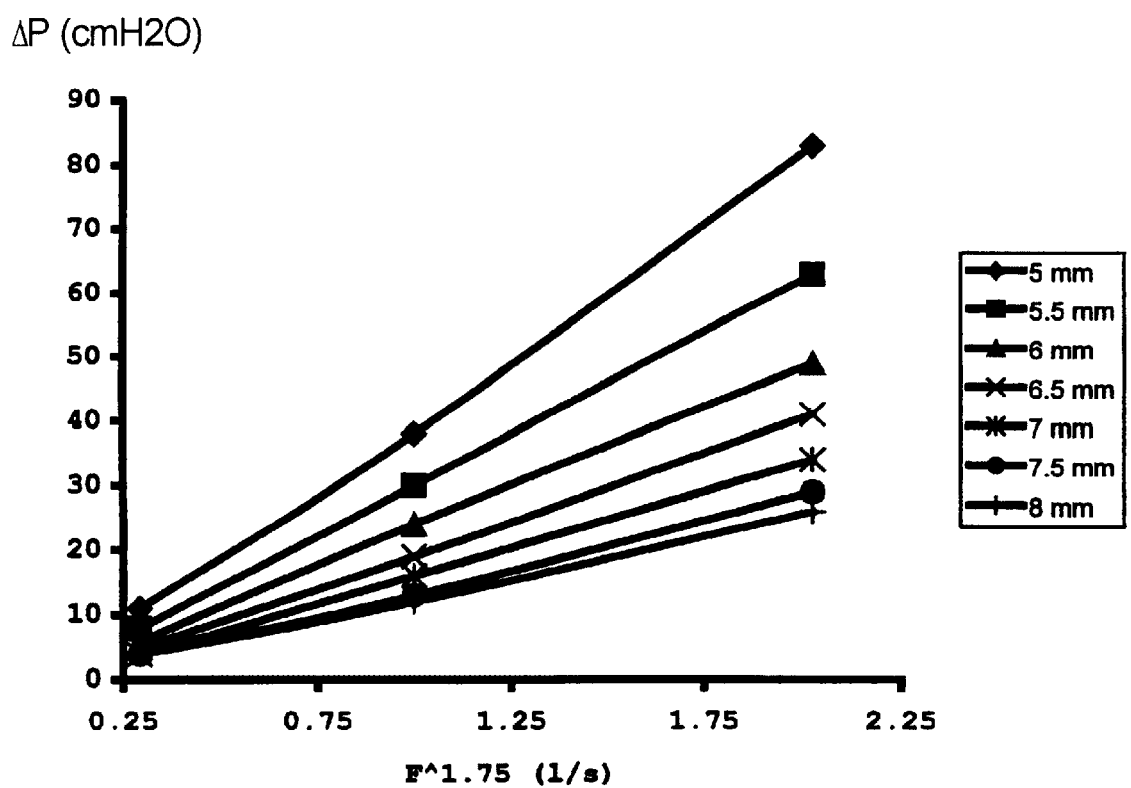
FIG. 4 shows the effect of the tube diameter on effective resistance of a breathing tube evaluated according to the breath-hold technique of FIGS. 2a and 2b.

The effect of breathing tube internal diameter on the calculated pressure drop $\Delta P$, as determined from breath-hold measurements described above, is shown in FIG. 4 for different inspiration flows F. The relationship is shown in FIG. 4 as a plot of $\Delta P$ with $F^{1.75}$.

Figure 5:
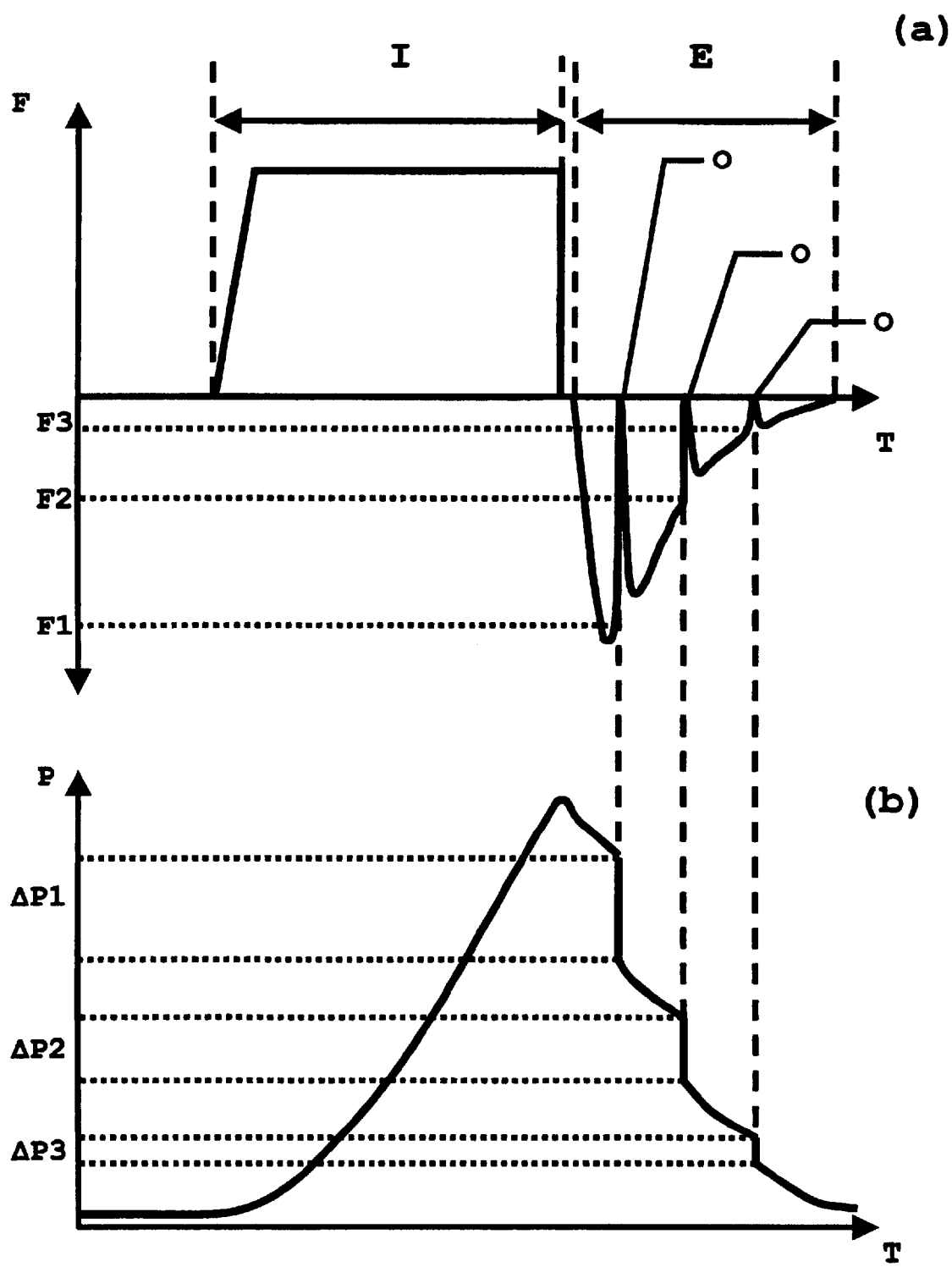
FIG. 5 illustrates at (a) gas flow characteristics during a breathing cycle in which temporary occlusions are introduced throughout an expiration phase, and illustrates at (b) corresponding gas pressure characteristics.

Additionally or alternatively the effective flow resistance of the breathing circuit 4 may be evaluated during on or more expiration phases of mechanical breathing assistance such as during a single expiration phase as shown with reference to FIG. 5.

The gas flow control unit 8 of the ventilator 2 is arranged to control the gas flow through the breathing circuit 4 to provide the patient with a breathing cycle comprising an inspiration phase I and an expiration phase E, with or without a breath-hold B, according to the requirements of the patient. After the inspiration phase 1, the unit 8 operates to close the inspiration valve 14 and open the expiration valve 16 in order to provide an expiration phase E. At the same time a trigger signal is passed from the flow control unit 8 to the control unit 28 of the calculation unit 6 to indicate the onset of the expiration phase E. After a predetermined time (or flow as measured by the sensor unit 34) the control unit 28 operates to supply a signal to the actuator 20 to close the expiration valve 16 and an initiate an occlusion O, to the flow of gas through the breathing circuit 4. A pressure P1, as measured by the sensor unit 34 is passed via the control unit 28 to the processor unit 30 where it may be stored in the memory 36 together with an associated gas flow value F1, as also measured by the sensor unit 34. A short time later (1 ms to 200 ms) the control unit 28 controls the actuator 20 to open the expiration-valve 16 and remove the occlusion. At this time second pressure P1', as measured by the sensor unit 34 is passed via the control unit 28 to the processor unit 30 which can then calculate a value of a pressure drop $\Delta P1$ (P1–P1') which is stored in memory 32 together with the flow value F1. These steps may be repeated at least once during the expiration phase E, and pressure drops P2, P3 calculated and stored in memory 32 together with their associated flow values F2, F3.

Alternatively, if more than one pressure drop $\Delta P$ is to be used to establish the relationship then at least one other expiration phase E, can be employed in at least one other breath. The occlusion O, is then introduced at a different predetermined time or measured flow.

Figure 6:
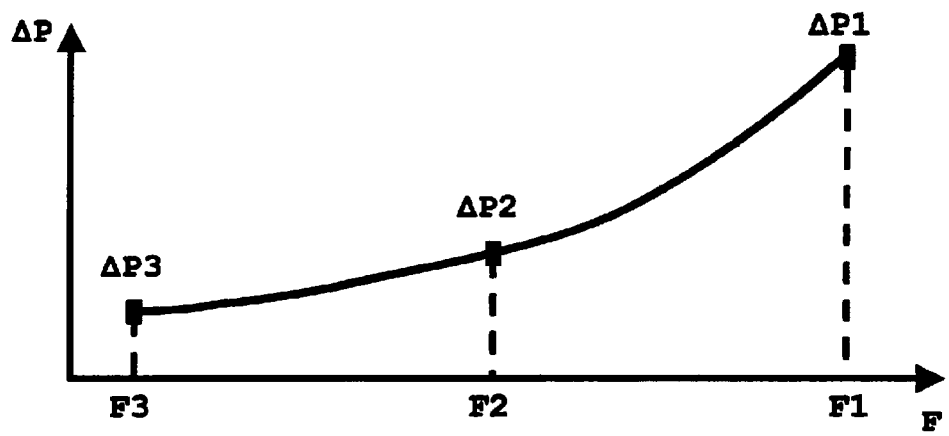
FIG. 6 shows an established relationship between pressure drops $\Delta P$, and gas flow F evaluated according to the expiration occlusion technique illustrated in FIGS. 5a and 5b.

The processor unit 30 may be adapted to recall the stored $\Delta P$ and F values and evaluate an effective flow resistance using these recalled values as described above in relation to the breath-hold process. Additionally or alternatively the processor unit 30 can establish a relationship between the pressure drops and flow values as an evaluation of the effective flow resistance by constructing a digital representation of the pressure drop($\Delta P$)/flow(F) curve illustrated in FIG. 6. The processor unit 30 can be programmed to establish a "best-fit" to the so determined curve using either previously stored curves for breathing tubes of known internal diameter or calculated using equation (3). The value of the breathing tube diameter giving the best fit can then be used by the gas flow control unit 8 of the ventilator 2 during the provision of breathing assistance to compensate measured pressures for the effects of the breathing tube resistance.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for evaluating an effective flow resistance of a breathing circuit during mechanical breathing assistance, comprising the steps of:

introducing a temporary occlusion to gas flow within a breathing circuit during a patient breathing cycle;

obtaining a flow value of gas flow in said breathing circuit which exists at a time of introduction of said occlusion;

determining a pressure drop within said breathing circuit resulting from introduction of said occlusion into said breathing circuit; and evaluating effective flow resistance in said breathing circuit by establishing a relationship between said pressure drop and said flow value.

2. A method as claimed in claim 1 wherein the step of establishing said relationship comprises determining a value of said pressure drop divided by the 1.75 power of said flow value.

3. A method as claimed in claim 1 comprising conducting the steps of introducing said temporary occlusion, obtaining said flow value and determining said pressure drop for a first gas flow, and subsequently repeating the steps of introducing said temporary occlusion, obtaining said flow value and determining said pressure drop for a second gas flow different from said first gas flow.

4. A method as claimed in claim 3 wherein the step of evaluating the effective flow resistance comprises determining a linear rate of change of the respective pressure drops for said first and second gas flows relative to the respective flow values, to the 1.75 power, for said first and second gas flows.

5. A method as claimed in claim 1 wherein the step of introducing a temporary occlusion comprises introducing said occlusion in said breathing gas circuit for a time period, and wherein the step of determining the pressure drop comprises measuring a circuit pressure which exists in said breathing circuit before introduction of said occlusion and a circuit pressure which exists in said breathing circuit at an end of said time period, back extrapolating said pressure at said end of said time period to determine a pressure at a beginning of said time period, and subtracting the pressure at the beginning of said time period from said circuit pressure which exists before introduction of said occlusion.

6. A method as claimed in claim 1 wherein the step of introducing a temporary occlusion comprises initiating a breath-hold at an end of an inspiration phase.

7. A method as claimed in claim 1 wherein the step of introducing a temporary occlusion comprises occluding gas flow in said breathing circuit during an expiration phase of a breathing cycle.

8. An arrangement for evaluating an effective flow resistance of a breathing circuit connected to a mechanical breathing assist device, said arrangement comprising:

a flow controller operable for temporarily introducing an occlusion to a gas flow within a breathing circuit at a time before an end of an inspiration phase of a breathing cycle provided by said breathing assist device;

a flow sensor for measuring gas flow within said breathing circuit;

a pressure circuit for measuring gas pressures within said breathing circuit; and an evaluation unit connected to said flow sensor and to said flow sensor for receiving measurement signals therefrom, said evaluation unit determining, For a measured gas flow, a value of a pressure drop within said breathing circuit resulting from the introduction of the occlusion, and for establishing a relationship between said pressure drop and said measured gas flow as an indicator of flow resistance in said breathing circuit.

* * * * *